United States Patent
Clock et al.

(10) Patent No.: US 11,980,702 B2
(45) Date of Patent: May 14, 2024

(54) SCENT DIFFUSING DEVICE

(71) Applicant: Aeron Lifestyle Technology, Inc., Fairfield, IA (US)

(72) Inventors: Jerome L. Clock, Hampton, IA (US); Patrick Guerin, Fairfield, IA (US); Monica Herr Hadley, Fairfield, IA (US); Ellora Hans-Price, Fairfield, IA (US)

(73) Assignee: Aeron Lifestyle Technology, Inc., Fairfield, IA (US)

( * ) Notice: Subject to any disclaimer, the term of this patent is extended or adjusted under 35 U.S.C. 154(b) by 907 days.

(21) Appl. No.: 16/286,760

(22) Filed: Feb. 27, 2019

(65) Prior Publication Data

US 2020/0268923 A1    Aug. 27, 2020

(51) Int. Cl.
*A61L 9/03*    (2006.01)

(52) U.S. Cl.
CPC ............. *A61L 9/03* (2013.01); *A61L 2209/12* (2013.01); *A61L 2209/135* (2013.01)

(58) Field of Classification Search
CPC ........... A61L 2209/12; A61L 2209/133; A61L 2209/135; A61L 9/03
USPC ........................................................ 392/394
See application file for complete search history.

(56) References Cited

U.S. PATENT DOCUMENTS

| | | | | |
|---|---|---|---|---|
| 2,595,010 A * | 4/1952 | Simpson | ................ | A47G 19/26 220/366.1 |
| 4,968,456 A * | 11/1990 | Muderlak | ................ | A61L 9/122 261/DIG. 65 |
| 5,394,506 A * | 2/1995 | Stein | ........................ | A61L 9/03 219/202 |
| 5,572,800 A * | 11/1996 | West | ........................ | A61L 9/03 34/390 |
| 6,241,161 B1 * | 6/2001 | Corbett | ............... | A01M 31/008 239/57 |
| 6,374,044 B1 * | 4/2002 | Freidel | ................ | B60H 3/0007 239/34 |
| 6,471,193 B2 * | 10/2002 | Cole Warren | ............ | A61L 9/12 261/95 |
| 6,805,300 B2 * | 10/2004 | Munroe | ................... | A61L 9/03 239/34 |
| 8,320,751 B2 * | 11/2012 | Porchia | ................... | A61L 9/032 392/386 |
| 9,220,302 B2 * | 12/2015 | DePiano | .................. | H05B 3/44 |
| 9,522,208 B2 * | 12/2016 | Esses | ...................... | A61L 9/032 |
| 9,931,424 B2 * | 4/2018 | Esses | ...................... | H05B 3/03 |
| 10,034,953 B2 * | 7/2018 | Bourne | ................ | B01F 23/215 |

(Continued)

OTHER PUBLICATIONS

FR2626452 (Aug. 1989) (Year: 1989).*
EP1076014 (Year: 2023).*
FR2626452—English translation.

*Primary Examiner* — Nathaniel E Wiehe
*Assistant Examiner* — Frederick F Calvetti
(74) *Attorney, Agent, or Firm* — ZarleyConley PLC

(57) ABSTRACT

A scent diffusing device having a first housing connected to a second housing and adapted to provide electrical power to a heating element disposed within the second housing. A cap assembly is removably attached to the second housing. The cap assembly has a support member removably attached to a cover, and a fragrance emitting member removably received within the support member. The support member has a central hollow tube that slidably receives the heating element.

14 Claims, 8 Drawing Sheets

(56) References Cited

U.S. PATENT DOCUMENTS

| | | | |
|---|---|---|---|
| 10,215,429 B2 * | 2/2019 | Blackley | A61L 9/035 |
| 10,624,980 B2 * | 4/2020 | Ye | A61L 9/03 |
| 10,869,501 B2 * | 12/2020 | Thorens | H05B 3/58 |
| 10,994,042 B2 * | 5/2021 | Westphal | A61L 9/03 |
| 11,083,812 B2 * | 8/2021 | Young | B60H 3/0014 |
| 11,097,032 B2 * | 8/2021 | Gao | A61L 9/14 |
| 11,192,051 B2 * | 12/2021 | Yamauchi | B01D 46/0049 |
| 11,497,825 B2 * | 11/2022 | Young | A61L 9/03 |
| 2006/0221594 A1 * | 10/2006 | Thuot Rann | A61L 9/037 |
| | | | 362/253 |
| 2006/0237439 A1 * | 10/2006 | Norwood | A01M 1/2077 |
| | | | 219/506 |
| 2009/0196587 A1 * | 8/2009 | Cheung | A61L 9/037 |
| | | | 392/394 |
| 2012/0199665 A1 * | 8/2012 | Neumann | A01M 1/2077 |
| | | | 239/135 |
| 2014/0133841 A1 * | 5/2014 | Hsiao | A61L 9/16 |
| | | | 392/386 |
| 2014/0261408 A1 * | 9/2014 | DePiano | A24F 40/46 |
| | | | 128/202.21 |
| 2014/0290650 A1 * | 10/2014 | Ivey | A24F 40/00 |
| | | | 392/404 |
| 2015/0117842 A1 * | 4/2015 | Brammer | A24F 40/48 |
| | | | 392/394 |
| 2016/0022857 A1 * | 1/2016 | Esses | A61L 9/032 |
| | | | 392/390 |
| 2016/0256585 A1 * | 9/2016 | Esses | H05B 3/03 |
| 2017/0112955 A1 * | 4/2017 | Bourne | A61L 9/125 |
| 2017/0128612 A1 * | 5/2017 | Roemburg | A61L 9/127 |
| 2018/0026932 A1 * | 1/2018 | Wang | H04W 68/12 |
| | | | 455/466 |
| 2018/0256770 A1 * | 9/2018 | Jang | A61L 9/12 |
| 2020/0188549 A1 * | 6/2020 | Gao | A61L 9/14 |

\* cited by examiner

SCENT DIFFUSING DEVICE

BACKGROUND OF THE INVENTION

The present invention is directed to a scent diffusing device and more particularly a scent diffusing device having an omnidirectional design with venting on all sides where the fragrance medium is heated from the inside and the fragrance medium is easily loaded with a no touch design.

Scent diffusing devices are known in the art. Typically, these devices have a fragrance pad that is positioned above a heating element and below a vent in a housing. Based on current designs, there are times when users insert the diffuser into a power source which reduces the effectiveness of the diffuser. In addition, to reload the pad, typically a liquid is poured onto the pad. During this procedure of removing the pad, loading the pad, and reinserting the pad, it is easy to get the liquid on one's hands. Therefore, there is a need in the art for a device that addresses these deficiencies.

As a result, an objective of the present invention is to provide a scent diffusing device that has a design that reduces user error.

Another objective of the present invention is to provide a scent diffusing device having a no-touch design for loading a fragrant liquid.

A still further objective of the present invention is to provide a scent diffusing device where replacement pads are easily loaded and unloaded out of the device.

These and other objectives will be apparent to those skilled in the art based upon the following written description, drawings, and claims.

SUMMARY OF THE INVENTION

A scent diffusing device includes a first housing, a second housing, and a cap assembly. The first housing has electrical components disposed with and extending out of the first housing that are adapted to provide electrical power to a heating member disposed within the second housing. The first housing is partially disposed within and connected to the second housing. The heating member preferably has a rod-like shape.

The cap assembly includes a cover, a support member, and one or more fragrance emitting members and is removably attached to the second housing. The support member is removably attached to the cover and extends perpendicularly away from the cover. The support member includes a pair of spaced rings connected to one another by a plurality of elongated bars and a central hollow tube connected to the rings. The rings, elongated bars, and central hollow tube, form one or more chambers adapted to receive fragrance emitting members.

The central hollow tube slidably receives the heating member to heat the fragrance emitting members from the inside.

DETAILED DESCRIPTION OF THE PREFERRED EMBODIMENTS

Figure 1:
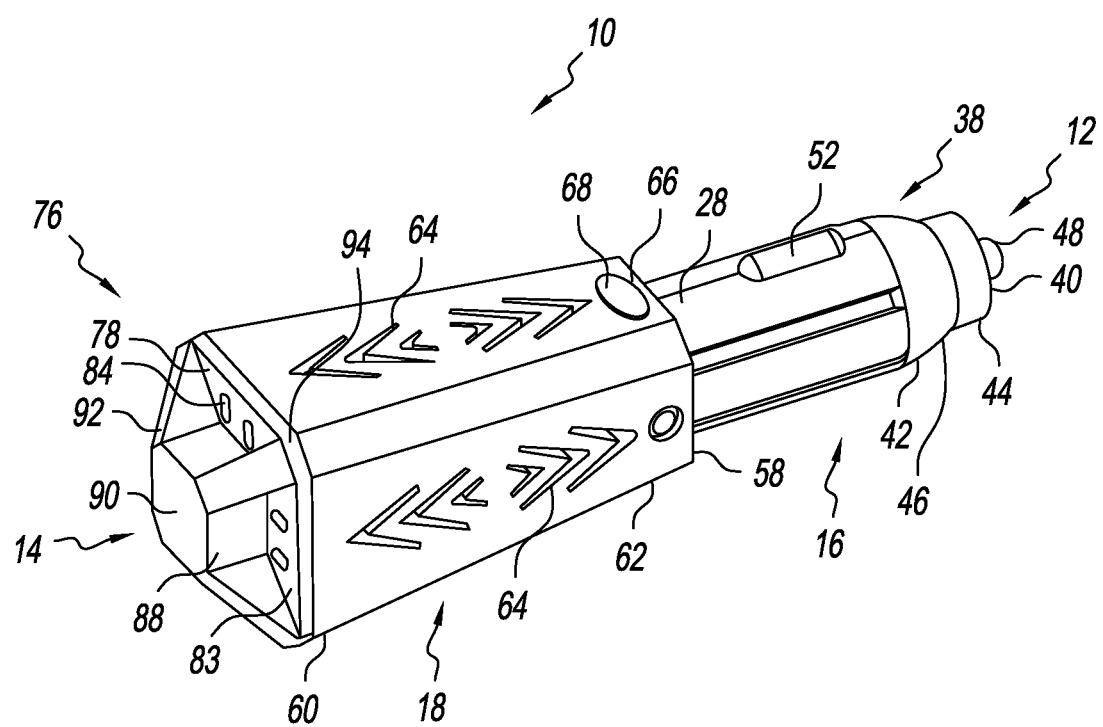
FIG. 1 is a perspective view of a scent diffusing device.
Figure 2:
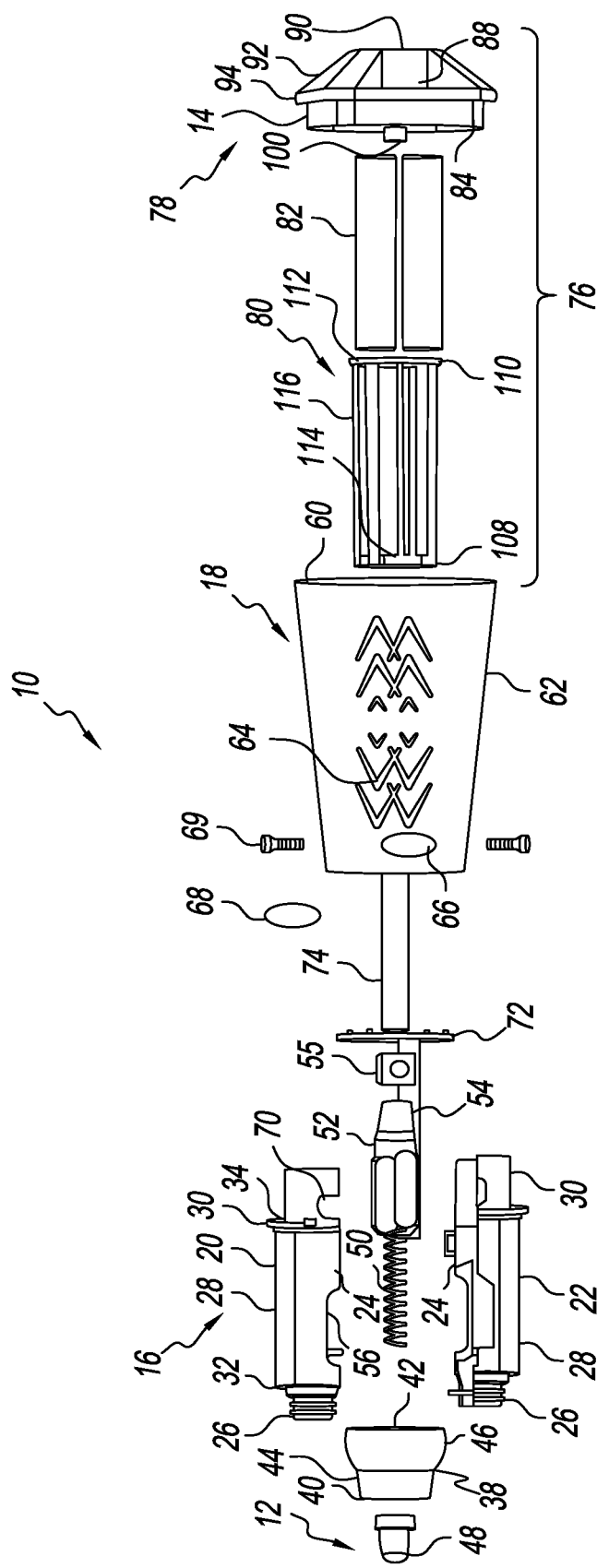
FIG. 2 is an exploded view of a scent diffusing device.
Figure 3:
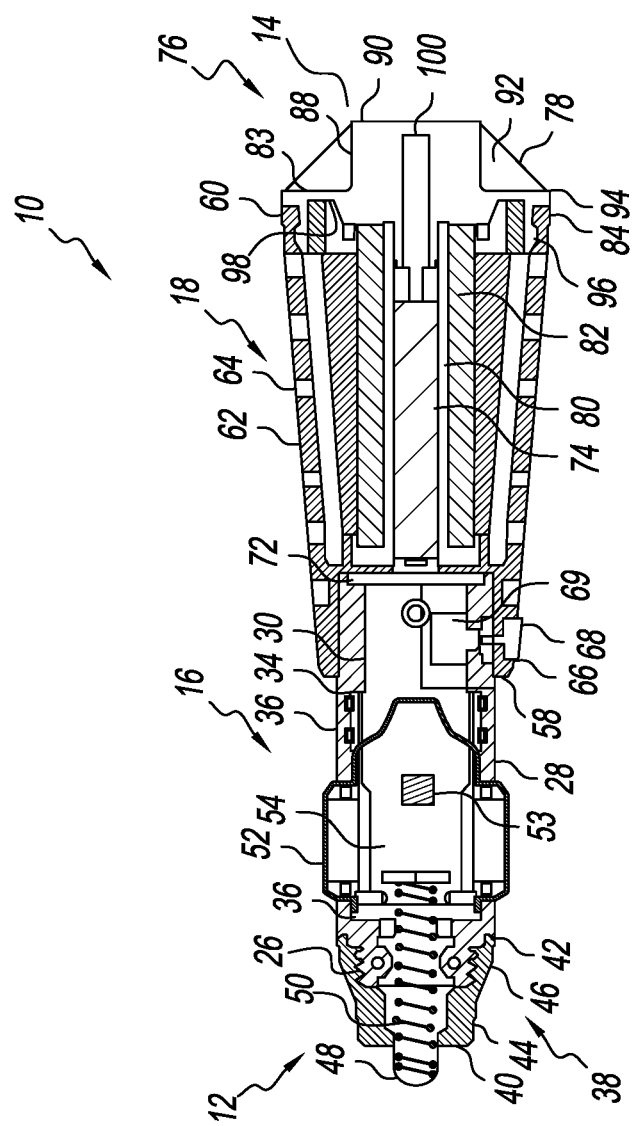
FIG. 3 is a side sectional view of a scent diffusing device.
Figure 4:
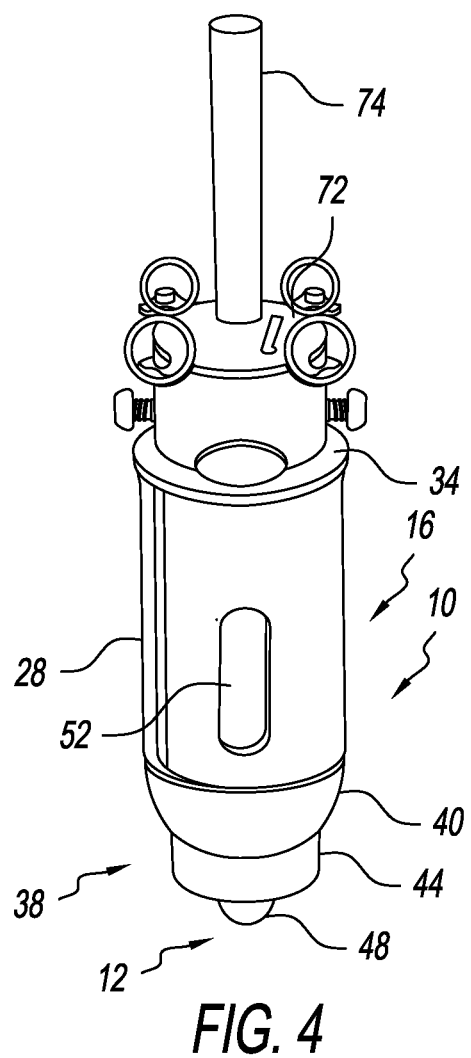
FIG. 4 is a partial perspective view of a scent diffusing device.
Figure 5:
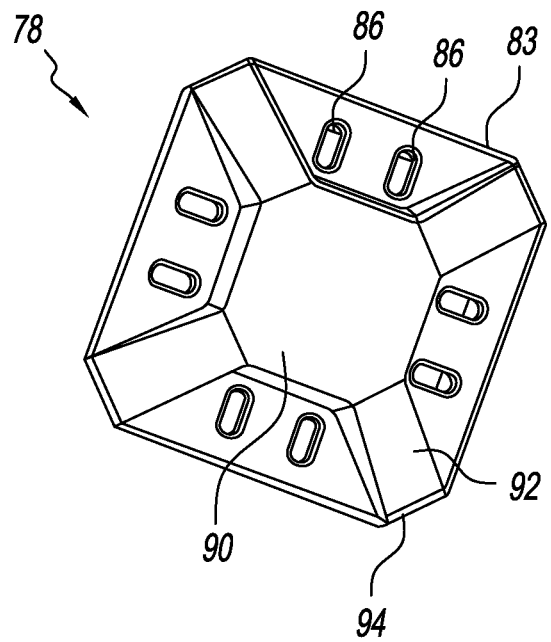
FIG. 5 is a top perspective view of a cover.
Figure 6:
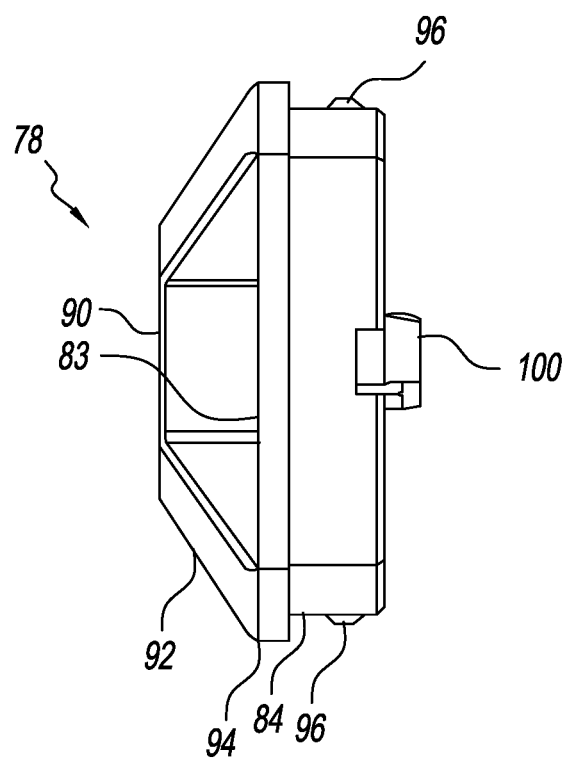
FIG. 6 is a side view of a cover.
Figure 7:
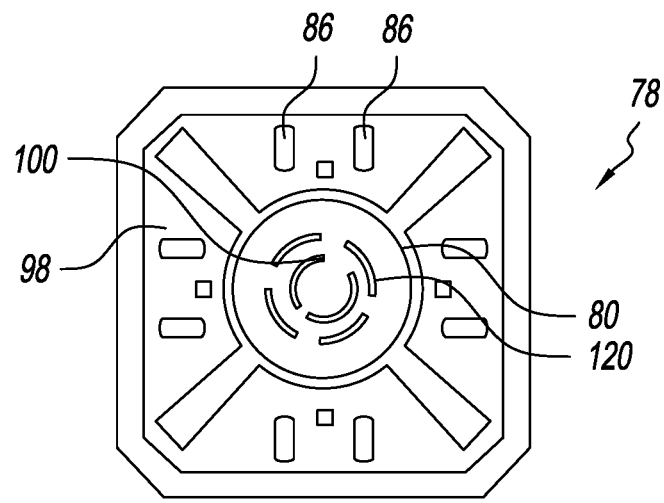
FIG. 7 is a bottom view of a cover.
Figure 8:
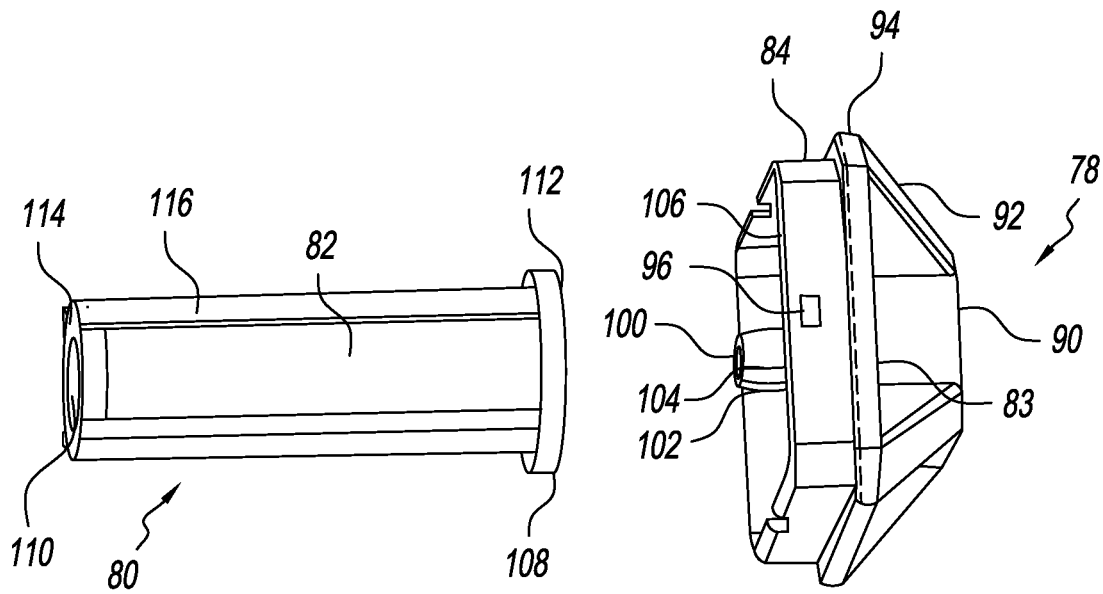
FIG. 8 is an exploded view of a cap assembly.
Figure 9:
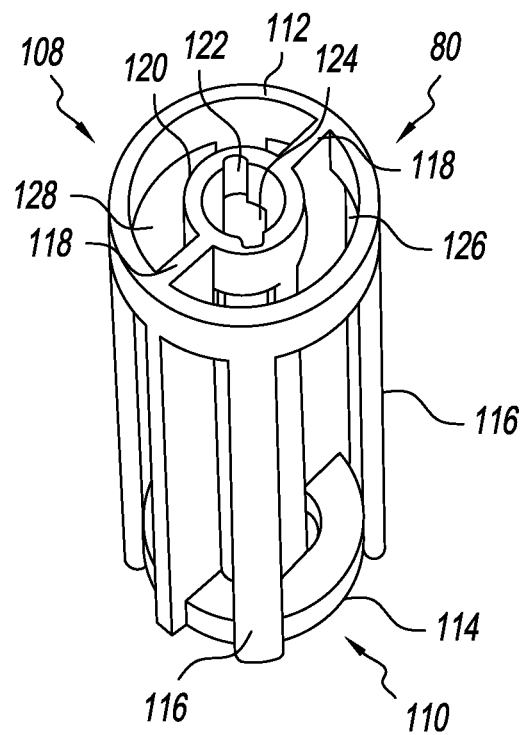
FIG. 9 is a perspective view of a support member.
Figure 10:
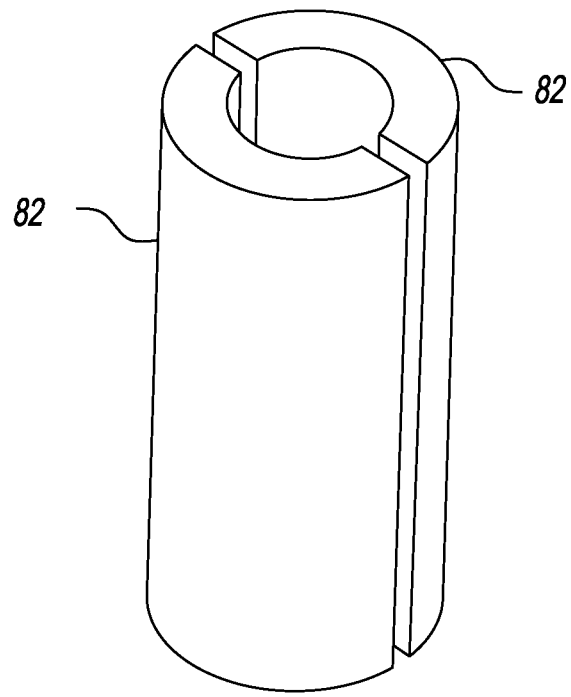
FIG. 10 is a perspective view of a fragrance emitting member.
Figure 11:
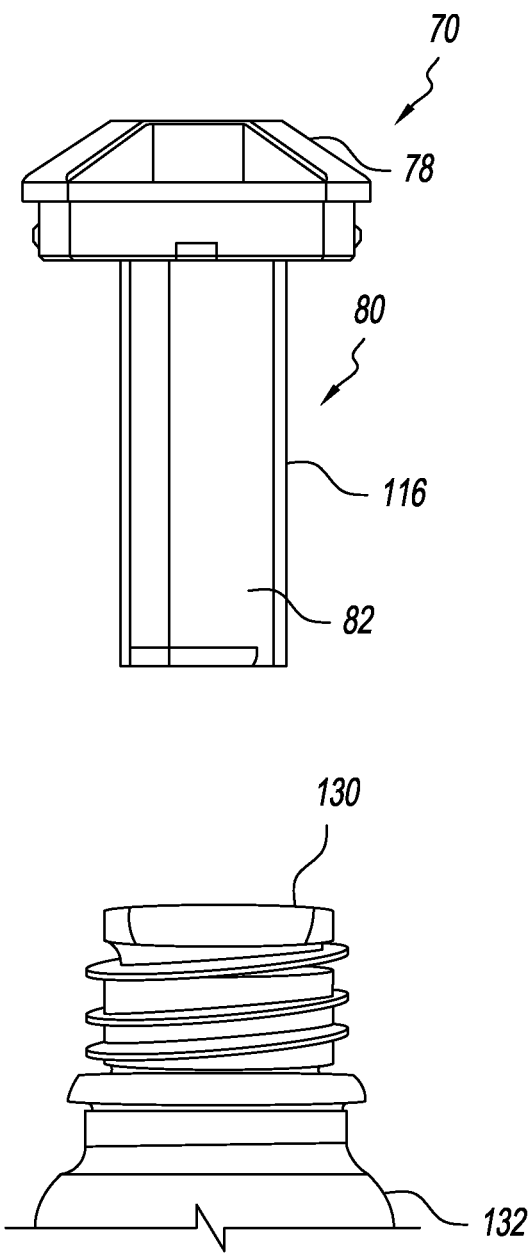
FIG. 11 is a side view of a cap assembly and a fragrance bottle.

Referring to the Figures, a scent diffusing device 10 has a first or forward end 12 and a second or rearward end 14. Adjacent the first end 12 is a first or forward housing 16 that is connected to a second or rearward housing 18.

The forward housing 16 preferably includes a first or upper cover 20 that is connected to a second or lower cover 22 along an elongated edge or seam 24. The covers 20 and 22 have a threadable first end 26, a cylindrical center section 28, and a rear end 30. The center section 28 has a diameter greater than the first end 26 and the second end 30 that form a first shoulder 32 and a second shoulder 34. The center section 28 has a protrusion 36 that forms part of the second shoulder 34.

Threadably connected to the first end 26 of the forward housing 16 is an end cover 38. The end cover 38 has a first end 40 and a second end 42. Adjacent the first end 40 is a generally cylindrical section 44 that terminates into a partial spherical section 46 adjacent the second end 42. Preferably, the diameter of the second end 42 is equal to the diameter of the center section 28 and the second end 42 engages the first shoulder 32 when the end cover 38 is threadably connected to the forward housing 16.

At the first end 40 of the end cover 38 is an opening adapted to receive a positive plate or electrode 48 that extends through the opening. Disposed within the forward housing 16 is a compressible spring 50, a negative plate or electrode 52, a circuit board 54, a timing chip 53, and an activation button 55. The spring 50 engages the positive plate 48 at one end and the circuit board 54 at the opposite end. The negative plate 52 is connected to the circuit board 54 and the circuit board is connected to the activation button 55. The center section 28 has cut-outs 56 that align with and receive negative electrodes 52. The assembled forward housing 16 is configured and adapted to be received within a 12-volt socket.

The rearward housing 18 has a first end 58, a second end 60, and a side wall 62. Preferably, the side wall 62 tapers inwardly as it extends from the second end 60 toward the first end 58. Cut through the side wall 62 are a plurality of air vents 64, and a button opening 66 having a button cover 68.

The rear end 30 of the forward housing 16 is received within the first end 58 of the rearward housing 18. The rear end 30 has an opening or cut-out 70 that aligns with the button 55 and the button opening 66.

Disposed within the rearward housing 18 is a second circuit board 72 that is connected to a heating member 74 such as a metal ceramic heater. The heating member 74 is elongated in order to maximize the affected surface area of fragrance emitting member 82. The second circuit board is electrically connected to the first circuit board 54. Removably attached to the second end 60 of the rearward housing 18 and partially disposed within the rearward housing is a cap assembly 76. The cap assembly 76 includes a cap or cover 78, and a fragrance emitting member 82 connected to the support member 80.

The cap 78 is of any size, shape, and structure. In one example, the cap 78 has a top 90, an end wall 83, and a side wall 84 that extends downwardly and perpendicularly from the end wall 83. Preferably, the end wall 83 has a plurality of air vents 86 disposed outside a raised portion 88. Preferably the raised portion 88 has a top surface 90 with a plurality of radial arms 92 that extend to angled corners 94. The side wall 84 has a plurality of nubs or detents 96 that extend outwardly from the side wall 84 and are positioned to provide a friction fit with an inner surface of the side wall 62 of the rearward housing 18.

An inner surface 98 of the cap 78 has a hollow tube 100 that is centrally positioned and extends perpendicularly away from the top surface 90 toward the rearward housing 18. The hollow tube 100 has a pair of outwardly extending projections 102 on an end section 104. The projections 102 extend from the end of the hollow tube 100 to a center section 106.

Removably connected to the cap 78 is the support member 80. The support member is of any size, shape, and structure. In the example shown, the support member 80 has a first end 108 and a second end 110. Positioned at the first end 108 and a second end 110 are a first ring 112 and a second ring 114 respectively. The rings 112 and 114 are connected to one another by a plurality of spaced elongated bars 116. Connected to the rings 112 and 114 and extending inwardly are a pair of aligned ribs 118. The ribs 118 extend from the rings 112 and 114 to a central hollow tube 120 that the ribs 118 are connected to. The hollow tube 120 is positioned to align with and receive heating member 74 and hollow tube 100.

At the first end 108 of the support member 80 the hollow tube 120 has a pair of slots 122 that are positioned to align with the projections 102 on hollow tube 100. The support member 80 is connected to the cover 78 by sliding tube 120 over tube 100 so that the projections 102 slide through the slots 122. Once the projections 102 are through the slots 122, the support member 80 is rotated in relation to the cap 78 so that the projections 102 catch on an inner shoulder 124 of hollow tube 120.

The hollow tube 120, rings 112 and 114, ribs 118, and elongated bars 116 form a pair of chambers 126 and 128. The chambers 126 and 128 are open at the first end 108 and are partially closed at the second end 110 by the width of the second ring 114. The chambers 126 and 128 are formed and adapted to receive fragrance emitting members 82 such as a pad or the like. The support member 80 has a length and a diameter adapted to fit within an opening 130 and extend through the length of a fragrance bottle 132.

In operation, while grasping the cap 78, the support member 80 is inserted through the opening 130 of and into the chamber of a fragrance bottle 132 filled with a fragrance liquid. The fragrance emitting members 82 absorb the liquid. The support member 80 is removed from the bottle 132 and the cap assembly 76 is attached to the rear housing 18. More specifically, the hollow tube 120 is slid over the heating member 74 and the cap 78 is inserted into the second housing 18 so that the nubs 96 on the side wall 84 of the cap 78 frictionally engage the inner surface of side wall 62 of rear housing 18 to seal the rear housing 18 closed.

The scent diffusing device 10 is inserted into a power supply (not shown) such as an automobile 12-volt socket. The diffusing device 10 is activated by depressing the button cover 68 which depresses button 55. Once activated, the circuit board 72 provides electricity to the heating member 74, until the timing chip 53 triggers a shutoff. The heating member 74 causes the liquid on the fragrance emitting members to evaporate so that a fragrant gas flows through the vents 64 on the side walls 62 of the rear housing 18 and into the atmosphere.

Accordingly, a scent diffusing device has been disclosed that at the very least, meets all the stated objectives. The device has an omnidirectional plug design with venting on all sides to reduce user error. The fragrance medium is heated from the inside instead of on a single side. Also, the device has a no touch design to load fragrance, and replaceable pads that load and unload easily.

What is claimed is:

1. A scent diffusing device, comprising:
a first housing having a positive and a negative electrode;
a second housing having a heating member;
the second housing having a sidewall with a plurality of vents;
a cap assembly having a support member;
the support member having a central hollow tube that slidably receives the heating member within the central hollow tube of the support member; and
the first housing having a first circuit board and the second housing having a second circuit board;
wherein the first circuit board is configured to activate the second circuit board and the second circuit board is configured to heat the heating member;
wherein the support member is removably connected to a cap.

2. The device of claim 1 wherein the cap assembly comprises the cap, the support member, a fragrance emitting member, and a tube that is centrally positioned on the cap and extends outwardly and perpendicularly to an end wall of the cap, wherein the tube is received within the central hollow tube of the support member.

3. The device of claim 1 wherein the cap is configured to frictionally engage an inner surface of a side wall of the second housing.

4. The device of claim 1 further comprising the first housing having a compressible spring, a circuit board, a timing chip configured to trigger a shutoff of the scent diffusing device, and an activation button configured to activate the scent diffusing device.

5. The device of claim 1 further comprising the first housing having a spring that engages the positive electrode at one end and a circuit board at the opposing end.

6. The device of claim 5 further comprising the negative electrode connected to the circuit board, wherein the circuit board is connected to an activation button.

7. The device of claim 1 further comprising the second housing having a button opening and a button cover, wherein the button opening is positioned to align with an activation button connected of the first housing when the first housing and second housing are assembled together.

8. A scent diffusing device, comprising:
a first housing having a positive and a negative electrode;
a second housing having a heating member;
a cap assembly having cap and a support member;
the cap having a sidewall, wherein the sidewall has a plurality of nubs that extend outwardly from the sidewall and are configured to provide a friction fit with an inner surface of a side wall of the second housing;
an inner surface of the cap having a hollow tube that extends perpendicularly away from a top surface of the cap towards the second housing; and
the hollow tube having a pair of outwardly extending projections on an end section, wherein the pair of projections extend from an end of the hollow tube to a center section, and wherein the projections are slidably received through slots on a hollow tube of the support member.

9. The device of claim 8 further comprising the sidewall of the cap extending downwardly and perpendicularly from an end wall of the cap.

10. The device of claim 8 further comprising a plurality of vents which are disposed outside a raised portion of the cap that is formed by a plurality of radial arms that each extend to corners the of the cap.

11. A scent diffusing device, comprising:
a first housing having a positive and a negative electrode;
a second housing having a heating member;
a cap assembly having a support member that receives the heating member and is configured to dispense a fragrant scent upon activation of the heating member; wherein the support member has a central hollow tube that slidably receives the heating member;
the support member having a first end with a first ring, and a second end with a second ring;
a plurality of spaced elongated bars that connect to and between the first ring and the second ring; and
a pair of aligned ribs that extend inwardly from the first ring and the second ring to the central hollow tube.

12. The device of claim 11 wherein the hollow tube, the first ring, the second ring, the plurality of spaced elongated bars, and the pair of aligned ribs form a pair of chambers; wherein the pair of chambers are open at a first end and partially closed at a second end, and the pair of chambers are configured to receive a fragrance emitting member.

13. The device of claim 11 further comprising the central hollow tube having a pair of slots that are positioned to align with a pair of projections on a hollow tube of a cap of the cap assembly.

14. The device of claim 13 wherein the cap is removably connected to the support member by rotating the cap in relation to the support member such that the projections of the hollow tube align with the pair of slots of the central hollow tube to allow removal; and to retain connection of the cap to the support member, the cap is rotatable to position the projections of the hollow tube against a shoulder within the central hollow tube when the projections are passed through the pair of slots.

\* \* \* \* \*